(12) United States Patent
Lee et al.

(10) Patent No.: US 6,423,343 B1
(45) Date of Patent: *Jul. 23, 2002

(54) BIOACTIVE GLASS TREATMENT OF INFLAMMATION IN SKIN CONDITIONS

(75) Inventors: Sean Lee; James L. Meyers, both of Gainesville, FL (US)

(73) Assignee: USBiomaterials Corporation, Alachua, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/012,272

(22) Filed: Jan. 23, 1998

(51) Int. Cl.⁷ .................. A61K 9/14; A61K 33/00; A61K 33/06; A61K 33/08; A61K 33/16

(52) U.S. Cl. .................. 424/489; 424/401; 424/601; 424/602; 424/606; 424/657; 424/660; 424/675; 424/688; 424/692; 424/722; 424/724; 424/400; 424/405; 424/484; 514/830; 514/859; 514/861; 514/862; 514/863; 514/864; 514/886; 514/887; 514/951

(58) Field of Search .................. 424/602, 400, 424/405, 484, 401, 489, 601, 606, 657, 660, 675, 688, 692, 722, 724; 514/830, 859, 861–865, 886, 887, 951

(56) References Cited

U.S. PATENT DOCUMENTS

| | | | |
|---|---|---|---|
| 4,103,002 A | 7/1978 | Hench | 428/155 |
| 4,272,518 A | 6/1981 | Moro et al. | 424/78.06 |
| 4,303,066 A | 12/1981 | D'Andrea | 602/52 |
| 4,538,603 A | 9/1985 | Pawelchak et al. | 602/56 |
| 4,539,200 A | 9/1985 | Quarfoot | 424/78.06 |
| 4,599,209 A | 7/1986 | Dautzenberg et al. | 264/7 |
| 4,613,502 A | 9/1986 | Turková et al. | 424/94.3 |
| 4,788,642 A | 11/1988 | Suzuki et al. | 395/299 |
| 4,837,285 A | 6/1989 | Berg et al. | 530/356 |
| 5,000,746 A | 3/1991 | Meiss | 604/304 |
| 5,290,544 A | 3/1994 | Shimono et al. | 424/63 |
| 5,352,715 A | 10/1994 | Wallace | 523/115 |
| 5,356,614 A | 10/1994 | Sharma | 430/37 |
| 5,501,706 A | 3/1996 | Arenberg | 623/16 |
| 5,591,453 A | 1/1997 | Ducheyne | 424/484 |
| 5,728,753 A | * 3/1998 | Bonfield et al. | 523/114 |
| 5,766,611 A | * 6/1998 | Shimono et al. | 424/401 |
| 5,834,008 A | * 11/1998 | Greenspan et al. | 424/443 |
| 5,840,290 A | * 11/1998 | Hench et al. | 424/423 |
| 6,086,374 A | * 7/2000 | Litkowski et al. | 433/217.1 |
| 2001/0041186 A1 | * 11/2001 | Greenspan et al. | 424/405 |

FOREIGN PATENT DOCUMENTS

WO 97/17401 5/1997

OTHER PUBLICATIONS

Embase Abstract, accession No. 76078548, 1975.*
Embase Abstract, accession No. 85063296, 1984.*
Hench, L. L. et al., "Biological Applications of Bioactive Glasses", *Life Chemistry Reports*, v13, p187–241, 1996.

* cited by examiner

*Primary Examiner*—John Pak
(74) *Attorney, Agent, or Firm*—Burns, Doane, Swecker & Mathis, L.L.P.

(57) ABSTRACT

This invention relates to a method for treating inflammatory symptoms such as burning, redness, itching, swelling and pain which accompany skin disorders other than wounds of the skin. The method comprising topical application of a topical medicinal composition comprising a non-interlinked, particulate bioactive glass mixed with a topical medicinal carrier to the site of the skin disorder.

7 Claims, No Drawings

BIOACTIVE GLASS TREATMENT OF INFLAMMATION IN SKIN CONDITIONS

FIELD OF THE INVENTION

This invention relates to a topical treatment and composition which may be applied to mitigate inflammatory symptoms such as burning, redness, itching, swelling and pain which accompany skin disorders, either of an acute or chronic nature.

BACKGROUND OF THE INVENTION

Many skin conditions, such as psoriasis, acne, poison ivy and heat rash to name only a few, are accompanied by an inflammation of the epithelium. This often leads to symptoms of burning, redness, itching, swelling and pain at the site. Although the root cause of the disorder varies with the disease, the generic inflammatory response is regulated by leukocyte activity and a host of inflammatory cytokines such as Interleukins and Tumor Necrosis Factors. Cell necrosis, as opposed to cell apoptosis, will release cellular debris into the extracellular environment in such a way as to activate neutrophils and macrophages, the key cells to initiate an inflammatory reaction. These activated cells themselves release a host of cytokines which chemotactically attract more leukocytes and other cells to the site of the inflammation. More information on inflammation, its causes, and its treatment may found in E. Arrigoni—Martelli *Inflammation and Antiinflammatories,* Spectrum Publication, 1977.

In recent years bioactive glasses have been used for a wide variety of health related applications (see Hench, et al., *Life Chemistry Reports* vol 13 pp 187–241 (1996)). Copending U.S. patent application Ser. No. 08/715,911, filed on Sep. 19, 1996, now U.S. Pat. No. 5,834,008, teaches a pharmaceutical composition comprising non-linked particles of bioactive glass, optionally in a carrier which is suitable for topical application. This composition is taught to be useful for promoting healing wounds and improving the structure and appearance of scar tissue as the wounds heal. However, there is no teaching that the composition could be used to reduce the symptoms of inflammation arising from skin disorders (other than wounds), such as allergic reactions and rashes.

SUMMARY OF THE INVENTION

The present invention is a method for treating inflammatory symptoms related to various skin disorders other than wounds, comprising topical application of a non-interlinked, particulate bioactive glass mixed with a topical medicinal carrier to the site of the skin disorder.

DETAILED DESCRIPTION OF THE PREFERRED EMBODIMENTS

As used herein the terms "bioactive glass" or "biologically active glass" mean an inorganic, glass material having an oxide of silicon as a major component and capable of bonding with growing tissue when reacted with physiological fluids. The term "skin disorder" means abnormalities, other than wounds, of the skin which have induced a state of inflammation. Such disorders include, but are not limited to warts acne, dermatitis, hives, psoriasis, rashes, contact allergic reactions, and reactions to insect stings, and bites.

The term "wound," as used herein, means an injury wherein the integrity of a patient's skin has been breached, as in the case of a cut or puncture, or where the skin has been destroyed by a chemical or thermal burn. "Normal" is used in the sense it is usually used in the medical arts. "Medical practitioner" means one of ordinary skill in the art of treating skin disorders. Typically this person is a physician, although in some cases, it may also be a nurse or physician's associate. The term "topical medicinal carrier" includes but is not limited to creams, ointments, gels, transdermal patches and lotions into which are blended therapeutic agents for topical application., Particulate bioactive glasses in accordance with the present invention typically have the following composition by weight percentage:

| Compound | percent range |
|---|---|
| $SiO_2$ | 40–86 |
| CaO | 10–46 |
| $Na_2O$ | 0–35 |
| $P_2O_5$ | 2–15 |
| $CaF_2$ | 0–25 |
| $B_2O_3$ | 0–10 |
| $K_2O$ | 0–8 |
| MgO | 0–5 | wherein the total composition is 100%

The preferred composition of the bioactive glass for the present invention by weight percentage is:

| Compound | Percent |
|---|---|
| $SiO_2$ | 45 |
| CaO | 24.5 |
| $Na_2O$ | 24.5 |
| $P_2O_5$ | 6 |

Bioactive glasses and methods of their preparation are well known in the art and several are commercially available.

Particulate, non-linked bioactive glass is preferred in the present invention. That is, the glass is in the form of small, discrete particles, rather than a fused matrix of particles or a fabric (woven or non-woven) of glass fibers. Note that under some conditions the discrete particles of the present invention may tend to cling together because of electrostatic or other forces but are still considered be The preferred particle size range for the bioactive glass is small and not greater than 90 microns. Particle sizes less than 20 microns as well as less than 2 microns can also be used. Particles of such a small size range generally provide for the advantages of the present invention but do not illicit any undesirable immune response.

There are many topical carriers know to those skilled in the art which may be used in the present invention, and the preferred carrier generally depends upon the specific disorder. The skilled artisans will appreciate that other therapeutic agents such as healing promotion agents, anti-inflammatory agents, antiseptic agents, and topical anesthetic agents may also be added to the composition of the present invention. Example of such agents include but are not limited to corticosteroids, benzocaine and lidocaine.

The bioactive glass and topical treatment can be combined in any pharmaceutically acceptable carrier to facilitate application to the skin. It is also within the scope of the present invention to combine the bioactive glass and topical ointment of the present invention with other treatments such as dressings, etc.

While not being bound to any particular theory or mechanism, the bioactive glass may also act as an absorbent of several inflammatory cytokines and thus act to shunt the overall inflammatory response in the area. Evidence indicates that reactivity of the bioactive glass releases ions into the extracellular environment which increases the extracellular osmotic pressure. This may reduce epithelial cell swelling and thus help prevent cell necrosis in the area, Most preferably, particulate bioactive glass and the carrier are mixed just before application to the skin. If the two ingredients are mixed several days prior to application, e.g. one week, the ability of the composition to mitigate the inflammation may be compromised. This problem is particularly acute, if the carrier causes bioactive glass to pre-react in a way that reduces the bioactivity of the glass.

While the ratio of bioactive glass to carrier is not critical, preferably the blend of bioactive glass, other therapeutic agents, and carrier contains about 20% to about 80% bioactive glass. The preferred particle size range for the bioactive glass is not greater about 90 microns is recommended. Particle sizes less than about 10 microns as well as less than about 2 microns can also be used. Particles of such a small size range generally provide for the advantages of the present invention but do not illicit any undesirable immune response. The proportion of other therapeutic agents varies according to the agent and the nature of the application. However, the preferred proportions are such that the amount of the agent administered to the area is in the dosage range approved by the accepted medical practice. The method of the present invention may be used on mammals, such as humans, and therefore is useful in both veterinary and well as human medicine.

The present invention is administered to a patient in a manner similar to that use for the administration of topical antiinflammatory compositions now in clinical use. While the exact treatment regimen is at the discretion of the attending medical practitioner, typical treatment comprises liberally applying a film of the bioactive glass containing composition to the inflamed area, optionally with gentle massage to work the composition into the skin. After application of the composition, the injured area is treated according to accepted medical practice, e.g., after applying the composition, the injured area may be covered with a sterile bandage. Of course, in nonhuman mammals treatment would be in accordance with accepted veterinary practice, but would typically be analogous to human treatment.

Treatment frequency is not critical but is typically two to four time daily although supplemental applications may be needed if the patient is active and prone to a high rate of perspiration. Treatment is continued until the attending medical practitioner determines the symptoms of the inflammation are no longer present. A patient being treated according to the method of the present invention may be concurrently treated with supplemental or adjuvant agents, such as oral or injected antiinflammatory or antibiotic agents.

EXAMPLES

Example 1

An individual suffering from psoriasis vulgaris and resulting prolonged inflammation on the arms was treated with a particulate bioactive glass known as "45S5" and having the preferred composition referenced herein above and having particle size of less than 20 microns blended into an aloe vera based gel. The ratio of bioactive glass to gel was 30 to 60 based on weight. These rashes were chronic and unsuccessfully treated prior to the treatment of this invention. The mixture of this invention was applied every 24 hours. After two treatments the itching, swelling and pain had ceased.

Example 2

An individual suffering for several years from psoriasis vulgaris on the palms of the hands was treated with a bioactive glass composition as used in Example 1. The rash was chronic and unresponsive to all other clinical treatments prior to the treatment of the present invention. The composition was applied once every 24 hours. After two treatments the itching, swelling and pain had ceased and redness was decreased.

Example 3

An individual suffering from a mildly chronic (18 month) skin rash on the top of the hand whose etiology was not determined was treated with a mixture of particulate bioactive glass composition described in Example 1. Previously, topical steroids alone were applied for 18 months with only moderate, transient success. The mixture of this invention was applied three times every 24 hours. After three reatments the rash had disappeared and did not recur.

What is claimed is:

1. A method of treating inflammatory symptoms related to skin disorders, other than wounds and burns, in a mammal, comprising topically applying to the site of the inflammatory skin disorder an inflammation treating amount of non-interlinked, particulate bioactive glass having a particle size range less than about 90 microns, the bioactive glass having the following compositional weight percentages:

| | |
|---|---|
| $SiO_2$ | 40–86 |
| $CaO$ | 10–46 |
| $Na_2O$ | 0–35 |
| $P_2O_5$ | 2–15 |
| $CaF_2$ | 0–25 |
| $B_2O_3$ | 0–10 |
| $K_2O$ | 0–8 |
| $MgO$ | 0–5. |

2. The method of claim 1, further comprising applying along with the bioactive glass, topical creams, ointments, gels, or lotions.

3. The method of claim 1, further comprising applying along with the bioactive glass, one or more additional therapeutic agents.

4. The method of claim 3 wherein one or more therapeutic agents are selected from the group consisting of healing promotion agents, anti-inflammatory agents, antiseptic agents, and topical anesthetic agents.

5. The method of claim 1, wherein the composition of the bioactive glass has the following compositional weight percentages:

| Compound | Percent |
|---|---|
| $SiO_2$ | 45 |
| $CaO$ | 24.5 |
| $Na_2O$ | 24.5 |
| $P_2O_5$ | 6. |

6. The method of claim 1, wherein the bioactive glass has a particle size range less than about 20 microns.

7. The method of claim 1, wherein the bioactive glass has a particle size range less than about 2 microns.

* * * * *